United States Patent
Pfeifer et al.

(10) Patent No.: US 8,648,316 B2
(45) Date of Patent: Feb. 11, 2014

(54) APPARATUS FOR COOLING SAMPLES DURING ION BEAM PREPARATION

(75) Inventors: Thomas Pfeifer, Zschopau (DE); Rainer Wogritsch, Vienna (AT)

(73) Assignee: Leica Mikrosysteme GmbH, Vienna (AT)

( * ) Notice: Subject to any disclaimer, the term of this patent is extended or adjusted under 35 U.S.C. 154(b) by 49 days.

(21) Appl. No.: 13/332,528

(22) Filed: Dec. 21, 2011

(65) Prior Publication Data

US 2012/0160471 A1   Jun. 28, 2012

(30) Foreign Application Priority Data

Dec. 23, 2010   (AT) .................................. A 2137/2010

(51) Int. Cl.
*G21K 5/08*   (2006.01)

(52) U.S. Cl.
USPC ................ 250/443.1; 250/440.11; 250/492.1; 216/41; 216/48; 216/87; 216/94; 216/58; 216/62; 216/63; 216/66

(58) Field of Classification Search
USPC ................ 216/41, 48, 58, 62, 63, 66, 87, 94; 250/440.11, 442.11, 443.1, 492.1, 250/492.2, 492.3
See application file for complete search history.

(56) References Cited

U.S. PATENT DOCUMENTS

| | | | |
|---|---|---|---|
| 3,171,957 A | 3/1965 | Coleraan | |
| 5,151,871 A * | 9/1992 | Matsumura et al. | 700/300 |
| 6,287,731 B1 * | 9/2001 | Katakura | 430/5 |
| 2005/0218336 A1 | 10/2005 | Mori | |
| 2006/0065853 A1 | 3/2006 | Rue et al. | |
| 2010/0025577 A1 | 2/2010 | Gruenewald et al. | |

FOREIGN PATENT DOCUMENTS

| | | |
|---|---|---|
| EP | 1852888 A1 | 11/2007 |
| GB | 2010557 A | 6/1979 |
| SU | 421908 | 3/1972 |

* cited by examiner

*Primary Examiner* — Nicole Ippolito
(74) *Attorney, Agent, or Firm* — Hodgson Russ LLP (57) ABSTRACT

The invention relates to a cooling apparatus (101) for a sample in an ion beam etching process, including, a sample stage (102) for arranging the sample, a coolant receptacle (120) containing a coolant, at least one thermal conduction element (106a, 106b) that connects the sample stage (102) to the coolant, a cooling finger (105) connected to the thermal conduction element (106a, 106b), the cooling finger (105) comprising a conduit (130, 131) through which coolant can flow and which is connectable to the coolant receptacle (120). The invention further relates to a method of adjusting the temperature of a sample in an ion beam etching process, including mounting a sample on a coolable sample stage (102), aligning the sample on the sample stage (102), and cooling the sample by coolant directed through a conduit (130, 131) of a cooling finger.

18 Claims, 7 Drawing Sheets

APPARATUS FOR COOLING SAMPLES DURING ION BEAM PREPARATION

CROSS REFERENCE TO RELATED APPLICATIONS

This application claims priority of Austrian patent application number A 2137/2010 filed Dec. 23, 2010, the entire disclosure of which is incorporated by reference herein.

FIELD OF THE INVENTION

The invention relates to a cooling apparatus for a sample in an ion beam etching process.

BACKGROUND OF THE INVENTION

Ion beam etching is a process often utilized to prepare samples whose structure is then typically investigated by scanning electron microscopy (SEM) and transmission electron microscopy (TEM). This technology is used in particular in research, materials research, and quality control for many materials, such as semiconductors, metals, ceramics, plastics, and the like. To carry out the process, the samples are mounted on a sample stage of an ion beam etching unit, and aligned in the beam path of one or more electron beams. Ion beam etching units are typically high-vacuum units that work with a baseline pressure of 10-6 mbar. The ions most commonly used are argon ions, usually at an acceleration voltage from 1 to 10 kV. The quality of the image resolution in the electron microscope is very substantially dependent, in this context, on the quality of the sample. Among the known ion beam etching processes known in practice are, in particular, ion beam slope etching, ion polishing of SEM samples, the wire shadowing method, and ion beam preparation of standard TEM samples. While the last two methods are used for TEM samples, ion beam slope etching is used to prepare cross-sectional SEM samples. In slope etching, profiles of the sample are exposed using the ion beam, a region of the sample being protected, by a mask arranged on the surface of the sample or aligned with respect to the surface of the sample, from material removal by the ion beam. An ion beam slope etching process that has proven particularly effective for producing high-quality SEM samples is one in which at least two ion beams, preferably three ion beams, are guided onto the sample surface at a predefined angle to one another. This method is disclosed in WO 2008/106815 A2.

In all ion etching methods, and in particular in the case of the method from WO 2008/106815 A2, it is advantageous if the sample is cooled during the ion etching operation. Cooling of the sample allows higher beam power levels, which in turn makes possible (even with very sensitive samples) higher etching rates and consequently high efficiency together with excellent reliability and good sample quality.

Cooling operations are used in a plurality of ion beam etching units, and are utilized for SEM and TEM prepared specimens and for special preparation techniques such as the aforementioned ion beam slope etching method. The samples are usually produced at room temperature, and are consequently stable at room temperature. The principal goal of a cooling operation is therefore to prevent the sample from heating up during ion beam etching, for example in order suppress diffusion processes and structural changes. Sufficient cooling is particularly important for heat-sensitive samples made of organic materials, for example plastics.

In practice, essentially two cooling methods have become established. The first method uses a Peltier element, which is embodied to be small and space-saving but has too little cooling output for many applications. The second cooling method encompasses cooling using a coolant, in particular cooling with liquid nitrogen; it is notable for a high cooling output, but has the disadvantage that safety provisions must be observed with regard to the coolant. Most present-day ion beam etching units operate with the second cooling method, cooling being effected with a cooling apparatus of the kind recited initially. Many of the ion beam etching units on the market, in which the sample must be moved (rotation, oscillation) in order to prevent preparation artifacts, exhibit the problems of insufficient thermal contact between the coolant and sample, and limited temperature measurement of the sample.

A further problem results from the limited coolant supply. In some of the known ion beam etching units, the sample is transferred into the vacuum chamber by means of an air-lock device. For service, or if the sample can no longer be transferred out of the vacuum chamber due to inadvertent detachment from the sample stage, the vacuum chamber must be aerated. For this, the coolant reservoir vessel must be baked out in order to completely vaporize the coolant. For this reason, only a limited supply of coolant is used in the known units. Because moreover no fill level indication or monitoring of the coolant supply is present, the fill level must constantly be monitored and coolant must be replenished as necessary. The coolant supply would not be sufficient for unattended sample preparation over a longer period of time (e.g. overnight). Constant manual replenishment of the coolant necessitates complex safety provisions, such as wearing protective clothing.

SUMMARY OF THE INVENTION

It is therefore an object of the invention to eliminate the disadvantages known from the existing art. The intention in particular is to implement a cooling apparatus in which it is possible to operate cooled preparation processes automatically and over a longer period of time.

This object is achieved according to the present invention in that the cooling apparatus comprises a cooling finger that is connected in heat-transmitting fashion, preferably directly, to the thermal conduction element, the cooling finger comprising a conduit through which coolant can flow and which is connectable to the coolant receptacle.

Thanks to the invention, cooling of the sample stage can occur automatically by simply activating and deactivating the flow of coolant passing through the cooling finger. The result is that larger coolant receptacles having more capacity can also be used, since laborious evaporation of the coolant prior to aeration of the vacuum chamber is not necessary. In contrast to the existing art, specimen preparation over a longer period of time (e.g. overnight) is thereby possible. The capability of quickly activating and deactivating cooling furthermore shortens the ion beam etching process and contributes to making it efficient. Handling by the user moreover becomes substantially easier and more reliable, since because a greater capacity can be selected, there is no further need for constant fill level monitoring and constant coolant replenishment.

The coolable sample stage is embodied as a vacuum flange that is flange-mounted onto the vacuum chamber of the ion beam etching unit. The sample stage is connected to the cooling finger via at least one thermal conduction element, the cooling finger preferably projecting into the vacuum chamber. The cooling finger serves not only for heat transport but also as a vacuum-tight passthrough of the cooling apparatus. The cooling finger can be connected to the sample stage with only one thermal conduction element, but also with several, for example, two or three, thermal conduction elements.

The term "heat-transmitting" refers to a thermal contact between the coolant and the sample stage, imparted by way of the cooling finger and the at least one thermal element, that is sufficient to enable good heat transport and thus good cooling of the sample.

The coolant receptacle is typically a Dewar vessel, and can have a substantially greater capacity as compared with the coolant receptacle known in the existing art. The capacity selected is preferably at least large enough that a sample preparation operation is possible without replenishment of the coolant and supervision by an operator (e.g. overnight). In practice, coolant receptacles having a capacity of 20 liters or more have proven successful for this.

In order to control the flow of coolant through the conduit of the cooling finger, it is useful if the cooling apparatus comprises a means for controlling the coolant flow.

In a particularly preferred and easily controllable embodiment, the means for controlling the coolant flow is embodied as a coolant pump. Activation of the coolant pump begins cooling of the sample stage, and deactivation of the coolant pump ends it again. By means of the coolant pump, the flow rate of the coolant through the conduit of the cooling finger can moreover be easily and efficiently adjusted and controlled via the pump rotation speed.

In a further embodiment, the means for controlling the coolant flow can be embodied as a valve element. The valve element, however, enables only activation and deactivation of the coolant flow through the conduit of the cooling finger. Because the coolant is not actively directed through the cooling finger, the coolant receptacle must also be arranged higher up than the cooling finger. The embodiment having the coolant pump, with which the flow rate can moreover be controlled, is preferred for these reasons.

In a further embodiment, the means for controlling the coolant flow can be embodied as a combination of a coolant pump and valve element. Here the pump output is held constant, and the flow rate is regulated by opening a controllable valve, preferably a flow regulator.

In a preferred embodiment, the cooling finger is embodied in double-walled fashion, the cooling finger preferably encompassing an outer tube and an inner tube arranged in the outer tube. The coolant preferably flows through the inner tube into the cooling finger, and back out of it through the outer tube.

As depicted in more detail in FIG. 4 below, the thermal conduction element is preferably pressed into a contact sleeve at an end directed toward the cooling finger, and then fastened onto the cooling finger. Fastening can occur, for example, by bolting or clamping the contact sleeve onto the cooling finger. A good heat-transmitting connection, and consequently strong cooling of the sample stage, can be ensured in particular by planar contact of the contact sleeve with the cooling finger over a large area, and further by tight bolting or clamping. A good heat-transmitting connection is achievable, for example, with a contact area of 10×10 mm between the contact sleeve and cooling finger.

The minimum temperature achievable by means of cooling at the sample stage therefore depends not only on the coolant used, but also critically on the thermal conduction between the coolant and the sample stage. On the one side is the coolant, which flows through the conduit of the cooling finger and has a certain temperature, for example less than −195.8° C. in the case of liquid nitrogen. On the other side is the sample stage to be cooled, which is not completely thermally insulated and which is constantly having heat delivered to it from outside, e.g. by the ion sources, and is constantly "losing cold." Heat can also be lost at the transition points at which the thermal conduction element is connected to the sample stage and the cooling finger. In addition to the connection (already explained above) between the thermal conduction element and the cooling finger, the embodiment of the thermal conduction element itself is also significant. The thermal conduction element is consequently manufactured from a highly thermally conductive material, preferably copper. The thermal conduction element is preferably embodied in strip-shaped fashion. Larger cross sections are preferably selected for the thermal conduction strip, since they enable greater heat transport and therefore lower temperatures. In practice, cross sections of, for example, 1×6 mm$^2$ and 2×6 mm$^2$ have proven favorable, better heat transport being possible with the greater cross section of 2×6 mm$^2$.

In a particularly advantageous embodiment, at least one further thermal conduction element, which extends from the cooling finger to a mask holder device for a mask, is provided, the sample being positionable relative to the mask. Typically, the sample is positioned relative to the mask before the ion beam etching operation. With this embodiment, therefore, not only the sample stage along with the sample mounted on it, but also the mask holder device along with the mask, are cooled. Simultaneous cooling of the sample stage and the mask holder device prevents drift, resulting from thermal expansion, between the mask edge positioned relative to the sample and the sample positioned with respect to the mask edge. The properties of the thermal conduction element that connects the mask holder device and the cooling finger correspond to those of the thermal conduction element that connects the sample stage to the cooling finger. The cooling finger can be connected to the mask holder device using only one thermal conduction element, but also using several, for example two or three, thermal conduction elements. With regard to the cross section of the thermal conduction elements, a cross section of 2×6 mm$^2$ for the thermal conduction strip extending to the sample stage, and a cross section of 1×6 mm$^2$ for the thermal conduction strip extending to the mask holder, have proven favorable in practice for example, for homogeneous cooling of the sample stage and mask.

It has further proven to be advantageous if the conduit of the cooling finger opens into an evaporator block for evaporating the coolant flowing out of the cooling finger. The coolant is usefully a liquefied gas, in particular liquid nitrogen or liquid air. The coolant is consequently directed from the coolant receptacle through the conduit of the cooling finger, and from there on into the tubing system of an evaporator block. The coolant is evaporated in the evaporator block. This has the advantage that after passage through the evaporator block is complete, only small quantities of the liquid coolant, and preferably only gaseous coolant, are still present. If the cooling apparatus encompasses a coolant pump, the flow rate of the coolant can then be regulated, by way of the pump rotation speed of the coolant pump, so that only gaseous coolant then emerges from the evaporator block.

In an advantageous variant, a temperature measuring means for measuring the temperature of the evaporator block, and/or a heating element, are associated with the evaporator block.

In a further advantageous variant, a temperature measuring means for measuring the temperature of the sample stage, and/or a heating element, are associated with the sample stage.

It is advantageous in this context if the temperature of the sample stage and/or of the evaporator block is regulatable.

Usefully, the cooling apparatus therefore has associated with it a temperature regulation device for regulating the temperature of the sample stage and/or the temperature of the evaporator block, a signal corresponding to the temperature of the sample stage and/or to the temperature of the evaporator block being delivered to the temperature regulating device, which regulates the temperature of the sample stage and/or the temperature of the evaporator block to a definable value. The temperature of the mask, when cooling occurs simultaneously with the sample stage, exhibits a temperature behavior approximately identical to that of the sample stage. As already described above, this depends on the respective cross sections of the thermal conduction strips; the optimum cross sections can be ascertained by one skilled in the art on the basis of routine experiments. In this embodiment the mask temperature is coupled to the regulation of the sample stage temperature and does not need additional monitoring.

In a refinement, the mask holder also has a temperature measuring means associated with it in order to measure the temperature of the mask holder and the mask, this temperature likewise being regulated by means of the temperature regulating device. For reasons of simplicity, however, it is preferable not to associate a separate temperature measuring means with the mask, but instead to couple the mask temperature, as described above, to the regulation of the sample stage temperature.

In a first advantageous variant, the temperature regulating device regulates the temperature of the sample stage and/or of the evaporator block to a definable value by way of the pump rotation speed of the coolant pump.

In a second advantageous variant, the temperature regulating device regulates the temperature of the sample stage to a definable value by means of the heating element associated with the sample stage.

In many applications the temperature value will be selected to be as low as possible, and will be held at a constant level during the entire ion beam etching operation. It has been found, in experiments, that with the apparatus according to the present invention the sample to be prepared can be cooled to a temperature of less than −150° C.

The advantage of the second variant as compared with the first variant is that desired changes in temperature can be reacted to more quickly. The second variant is therefore utilized in particular in cases in which the temperature of the sample is intended to be substantially higher than the minimum temperature attainable by cooling, or if a change in sample temperature (e.g. a temperature gradient) during the ion beam etching operation is desired. Regulation of the sample temperature by way of the pump rotation speed of the coolant pump might prove too sluggish in these cases, and the second variant would therefore be preferable. One skilled in the art can decide for the specific case, based on apparatus parameters and optionally on the basis of simple routine experiments, whether the first or the second variant is better suited for a specific ion beam etching operation.

Most ion beam etching units described above in reference to the existing art do not provide any capability for controlled automatic sample heating after the ion beam etching operation. A risk therefore always exists of contaminating the sample with condensed water (dew) when the ion beam etching unit is aerated.

To prevent the sample from being contaminated after completion, upon aeration and opening of the sample stage flange, with water condensed from ambient air, it is advantageous if after completion of the ion beam etching operation, the temperature regulating device regulates the temperature of the sample stage and of the evaporator block, by means of the heating element associated with the evaporator block, to a temperature value at which condensation of atmospheric moisture from ambient air onto the sample is prevented. As already mentioned above, the mask exhibits a temperature behavior approximately identical to that of the sample stage. The coolant flow through the cooling finger is usually stopped before heating. Advantageously, the temperature is regulated to room temperature.

It is a further object of the invention to make available a method for adjusting temperature using the cooling apparatus according to the present invention.

This object is achieved according to the present invention with a method for adjusting the temperature of a sample in an ion beam etching process, the method encompassing the following steps:
(a) mounting a sample on a coolable sample stage of an ion beam etching apparatus, the sample stage having a previously described cooling apparatus associated with it, and aligning the sample on the sample stage; and
(b) cooling the sample by means of the coolant directed through the conduit of the cooling finger, a temperature desired for the ion beam etching operation being established.

The method preferably encompasses a step (c), following step (b), in which cooling of the sample is terminated after termination of the ion beam etching operation. For this, the delivery of coolant, which as described above can be controlled via a coolant pump or a valve, is stopped.

The method preferably further encompasses a step (d), following step (c), in which the sample is heated to a temperature at which condensation of atmospheric moisture from ambient air onto the sample is prevented. The sample is preferably heated to room temperature.

If the sample is aligned relative to a mask in an ion beam etching process, it is advantageous if the mask is cooled, and heated back to room temperature, analogously to the sample. As already mentioned, simultaneous cooling of the sample stage and of the mask holder device prevents drift, resulting from thermal expansion, between the mask edge positioned relative to the sample and the sample region positioned with respect to the mask edge. The temperature of the mask, when cooling and heating occur simultaneously with the sample stage, exhibits a temperature behavior approximately identical to that of the sample stage. The mask temperature is thus coupled to the sample stage temperature and does not need additional monitoring.

For most ion beam etching processes, provision is made that the temperature of the sample is held constant during the ion beam etching operation.

As already discussed above, the coolant is usefully a liquefied gas, preferably liquid nitrogen or liquid air. Liquid nitrogen is usually used in ion beam etching processes. In a preferred embodiment, the flow rate of the coolant is adjusted, for example via the pumping rate of the coolant pump, so that after flowing through the evaporator block, the coolant then emerges therefrom only in gaseous form. This firstly decreases the risk of the operator coming into contact with the liquefied gas, and secondly prevents excessive coolant consumption.

BRIEF DESCRIPTION OF THE DRAWINGS

Exemplary embodiments of the present invention are described in more detail below with reference to the schematic drawings, in which.

DETAILED DESCRIPTION OF THE INVENTION

Figure 1:
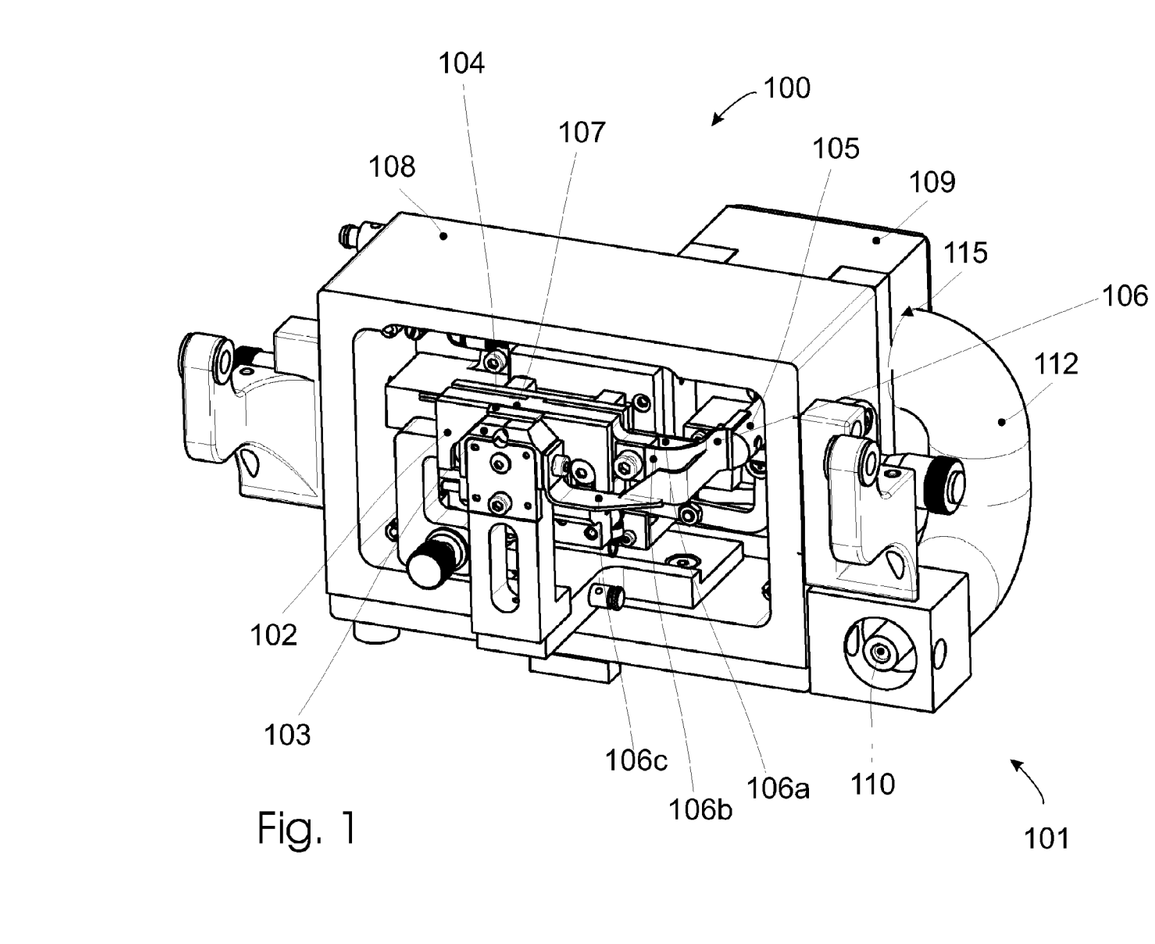
FIG. 1 is a perspective view of a sample stage flange having a cooling apparatus according to the present invention, looking toward the sample stage.

FIG. 1 shows a sample stage flange 100 that is designed for an ion beam slope etching process and has a cooling apparatus 101 according to the present invention associated with it. Sample stage flange 100 is mountable in vacuum-tight fashion onto an ion beam etching unit (ion beam etching unit 200, see FIGS. 5 to 7). Cooling apparatus 101 encompasses a coolable sample stage 102 on which the sample (not depicted) is mountable, as well as a coolable mask holder 103 having a mask 104. Cooling apparatus 101 further encompasses a cooling finger 105. Sample stage 102 and mask holder 103 are connected in heat-transmitting fashion to cooling finger 105 via thermal conduction strips 106a, 106b, 106c so that mask holder 103 and mask 104 are cooled simultaneously with sample stage 102 and the sample. The cross sections of thermal conduction strips 106a, 106b, 106c are selected in such a way that homogeneous cooling of sample stage 102 and mask holder 103 occurs. Thermal conduction strips 106a, 106b, 106c extend from a common origin 106 on cooling finger 105 to sample stage 102 (thermal conduction strips 106a, 106b) and to mask holder 103 (thermal conduction strip 106c). Before the ion beam etching operation begins, the sample is positioned relative to mask 104. Simultaneous cooling of sample stage 102 and mask holder 103 prevents drift, resulting from thermal expansion, between a sample positioned relative to mask edge 107 and the sample region positioned with respect to mask edge 107.

Sample stage 102, mask holder 103, thermal conduction strips 106a, 106b, 106c, and cooling finger 105 are arranged inside housing 108 of specimen stage flange 100. An evaporator block 109 is attached outside sample stage flange 100. Cooling finger 105, which is also connected to evaporator block 109, extends through housing 108 of sample stage flange 100 and is consequently embodied in vacuum-tight fashion. Cooling finger 105 is of double-walled configuration (see sectioned depiction through cooling finger in FIG. 4) and has coolant, which in this case is liquid nitrogen, flowing through almost its entirety.

Figure 2:
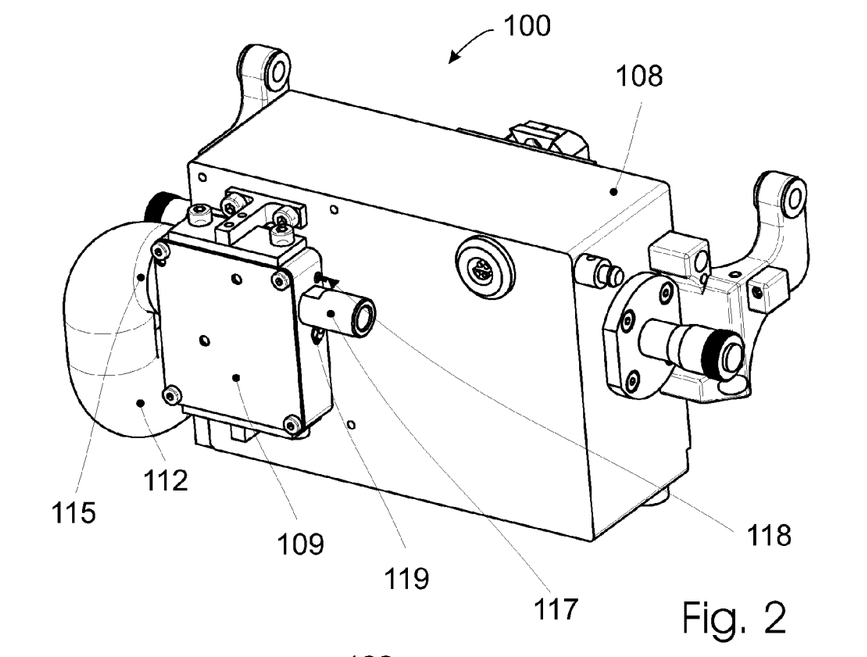
FIG. 2 shows the sample stage flange of FIG. 1, looking toward the evaporator block of the cooling apparatus.

The coolant is located in a reservoir receptacle 120 (Dewar vessel) and is pumped from there, by means of a coolant pump 121 (see FIG. 4) whose connector 110 is located on housing 108 of sample stage flange 100, through a jacketed coolant line 112 to inlet 115 of evaporator block 109. FIG. 2 is a rear view of sample stage flange 100 looking toward evaporator block 109. A temperature sensor 118 is arranged inside evaporator block 109 in order to monitor and regulate the temperature of evaporator block 109. Also arranged in evaporator block 109 is a heating element 119 that, after completion of the ion beam etching operation, serves to heat the entire sample stage flange 100 to, preferably, room temperature (see FIG. 12). From inlet 115 of evaporator block 109, the coolant is then directed into and back out of cooling finger 105. The coolant that is directed out flows through a tubing system 111 inside evaporator block 109 and is evaporated there, such that preferably only gaseous coolant (gaseous nitrogen) then emerges at outlet 117 of evaporator block 109. The flow path of the coolant through the cooling apparatus is described again below in detail in FIG. 4.

Figure 3:
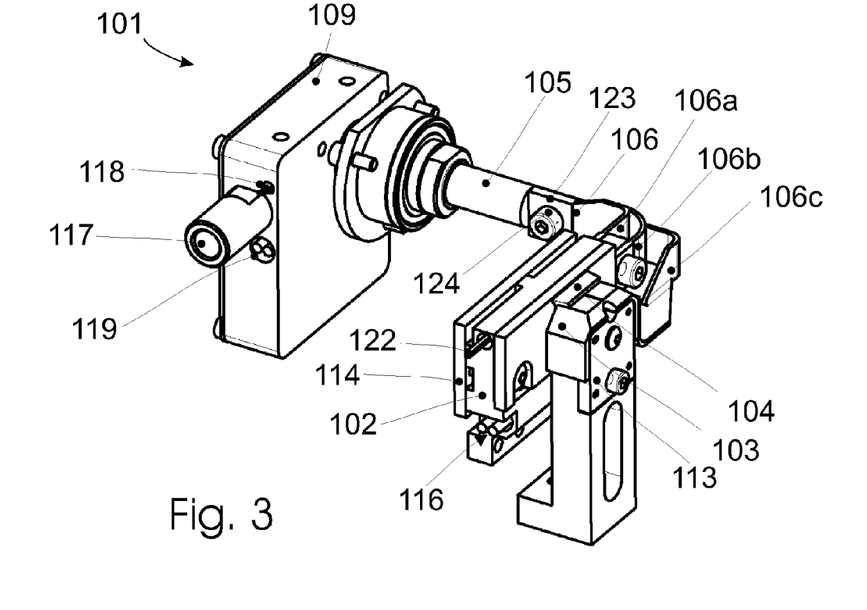
FIG. 3 is a perspective view of components of a cooling apparatus according to the present invention.

FIG. 3 presents a perspective view of components of cooling apparatus 101 according to the present invention as incorporated into sample stage flange 100. The components depicted encompass sample stage 102, mask holder 103 having mask 104 located thereon, evaporator block 109, cooling finger 105, and thermal conduction strips 106a, 106b, 106c. Thermal conduction strips 106a, 106b, 106c extend from common origin 106 on cooling finger 105 to sample stage 102 (thermal conduction strips 106a, 106b) and to mask holder 103 (thermal conduction strip 106c). Origin 106 of thermal conduction strips 106a, 106b, 106c is pressed into a contact sleeve 123 and is then fastened onto cooling finger 105 by means of a fastening screw 124. The contact area between contact sleeve 123 and cooling finger 105 is selected so that a good heat-transmitting connection is achievable. In the example shown, the contact area between contact sleeve 123 and cooling finger 105 is equal to approximately 10×10 mm. Further components of cooling apparatus 101, such as reservoir vessel 120 for the coolant as well as coolant pump 121, which are not depicted in FIG. 3, are depicted below in FIG. 4. Sample stage 102 and mask holder 103 are thermally insulated with respect to the other components of sample stage flange 100 by adjacent poorly thermally conductive elements 113, 114 in order to minimize heat loss. A temperature sensor 122 is also located inside sample stage 102 in order to monitor and regulate the temperature of sample stage 102. In addition, in the context of a variant control loop for regulating the temperature of sample stage 102 that is described later on (see FIG. 9), a heating element 116 is also arranged inside sample stage 102.

Figure 4:
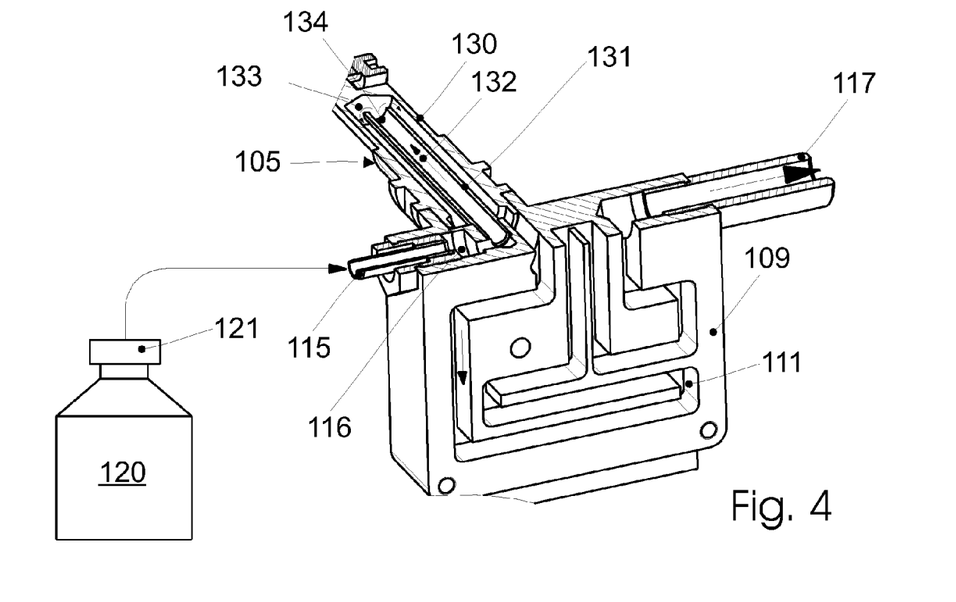
FIG. 4 depicts the flow path of coolant through the cooling apparatus.

FIG. 4 illustrates the flow path of coolant through cooling apparatus 100. The coolant is stored in a reservoir vessel 120. The capacity of reservoir vessel 120 is preferably selected to be at least large enough that sample preparation is possible without replenishing the coolant and monitoring by an operator (e.g. overnight). In practice, coolant receptacles having a capacity of 20 liters or more have proven successful for this. Before the ion beam etching operation begins, cooling of sample stage 102 and of mask holder 103 is started by switching on coolant pump 121. For this, the coolant is pumped by means of coolant pump 121 out of reservoir vessel 120 to input 115 of evaporator block 109, and through a cooling finger connector 116 toward the double-walled cooling finger 105. Cooling finger 105 encompasses an outer tube 130 and an inner tube 131 arranged in outer tube 130. The flow direction of the coolant is depicted by arrows 132, 133. The coolant (liquid nitrogen) flows through the inner tube into cooling finger 105 (arrow 132) and travels through a tube opening 134 of inner tube 131 into outer tube 130. From there it flows in an opposite direction (arrow 133) back out of cooling finger 105, and from there travels on into tubing system 111 of evaporator 109, where it is evaporated. The flow rate of the coolant is preferably regulated, by means of the pump rotation speed of coolant pump 121, so that after passage through tubing system 111, only gaseous coolant (gaseous nitrogen) then emerges at outlet 117 of evaporator block 109. Temperature regulation is explained in more detail later on. After of the ion beam etching operation ends, cooling is stopped by deactivating coolant pump 121, and all the cooled components of the sample stage flange are heated, preferably to room temperature, by means of heating element 119 of evaporator block 109.

Figure 5:
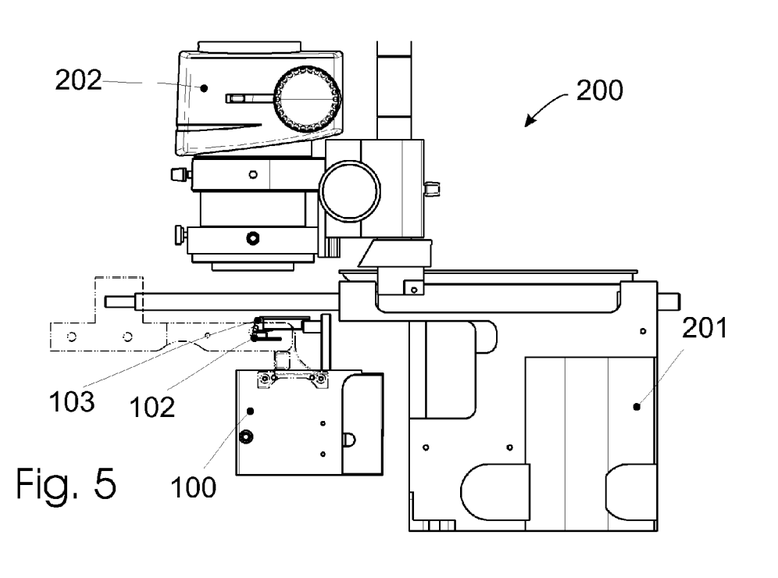
FIG. 5 is a side view of an opened ion beam etching unit, with the sample stage of FIG. 1 mounted therein, in an alignment position.
Figure 6:
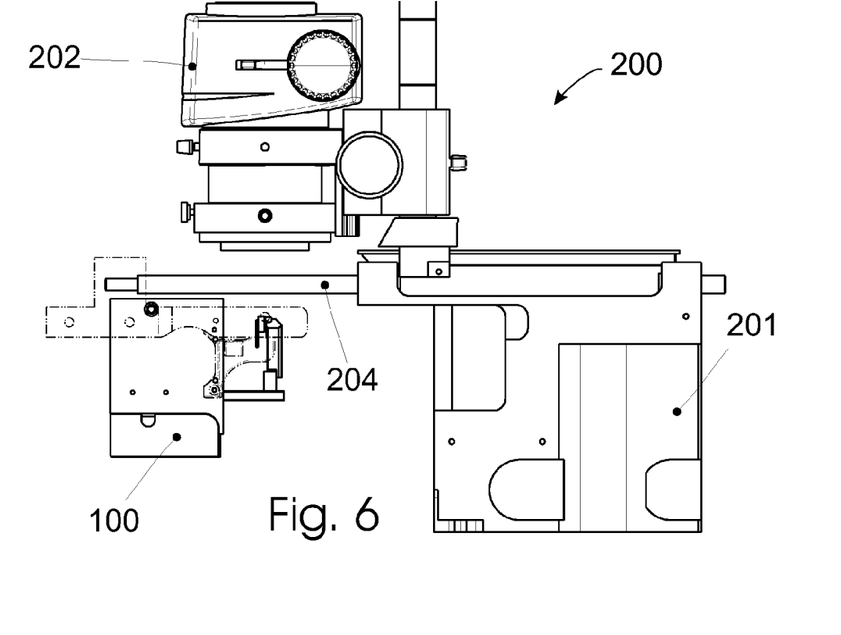
FIG. 6 shows the ion beam etching unit of FIG. 5, the sample stage flange being pivoted into the closed position.

FIGS. 5 and 6 each show side views of an opened ion beam etching unit 200 having sample stage flange 100 mounted therein. When ion beam etching unit 200 is set up, sample stage flange 100 is attached to vacuum chamber 201 (recipient) in which the ion sources are located (see FIG. 7, which shows a cross section through a closed vacuum chamber 201 with sample stage flange 100 attached). Returning to FIGS. 5 and 6: sample stage flange 100 is mounted tiltably through 90° for sample alignment. Before a vacuum is applied and before the ion beam etching operation begins, the sample is fastened on sample stage 102 and is aligned manually relative to the mask. In FIG. 5, sample stage flange 100 is in a first alignment position tilted 90°. In FIG. 6, sample stage flange 100 is in its second alignment position, this alignment position also representing the position in which sample stage flange 100 is then displaced horizontally, by means of a support rail 204, toward vacuum chamber 201 and attached thereto. Ion beam etching unit 200 further comprises a binocular 202 for sample alignment.

Figure 7:
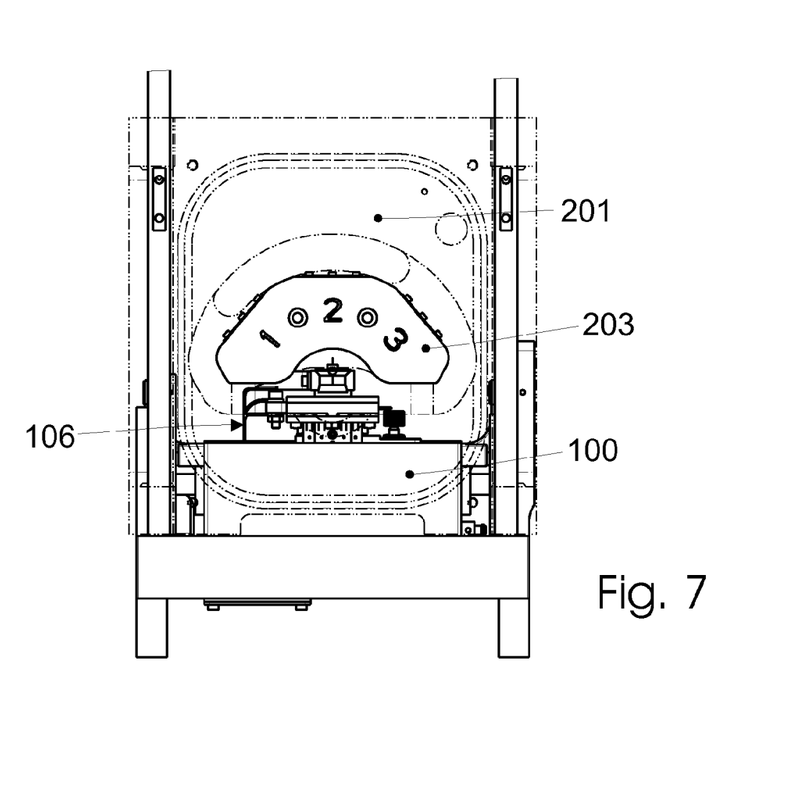
FIG. 7 is a section through the closed vacuum chamber of the ion beam etching unit of FIG. 5 and FIG. 6, the sample stage flange being in the operating position.

Once the sample has been loaded and aligned, sample stage flange 100 is attached to the recipient of ion beam etching unit 200, and the sample chamber is pumped down in order to create a high vacuum (usually at least 10-6 mbar). FIG. 7 is a plan view of a section through the closed vacuum chamber 201 with sample stage flange 100 attached. The etching process occurs in accordance with the ion beam slope etching method from WO 2008/106815 A2 recited above in the existing art; consequently, as described in WO 2008/106815 A2, three ion beams that are integrated into ion source 203 are guided onto the sample surface at a defined angle to one another.

Once the vacuum has been created in vacuum chamber 201, the sample is cooled to the desired temperature and is processed with the ion beams. During processing of the sample, the sample temperature is maintained constantly, by regulation, at a desired temperature value. When the sample has been completed, it is heated to a desired temperature value, preferably room temperature, in order to avoid contamination with condensed water when sample stage flange 100 is aerated and opened.

The control loops for regulating temperature during the ion beam etching process are described further in FIGS. 8 to 13 that follow. Cooling apparatus 101 has associated with it, for this purpose, a central temperature regulation device (Controller) that is responsible for regulating the control loops recited below, and variants thereof, during cooling and heating. The box labeled "Heat" in FIGS. 8 to 12 refers to the external thermal influences that act on sample stage 102 and evaporator 109.

Figure 8:
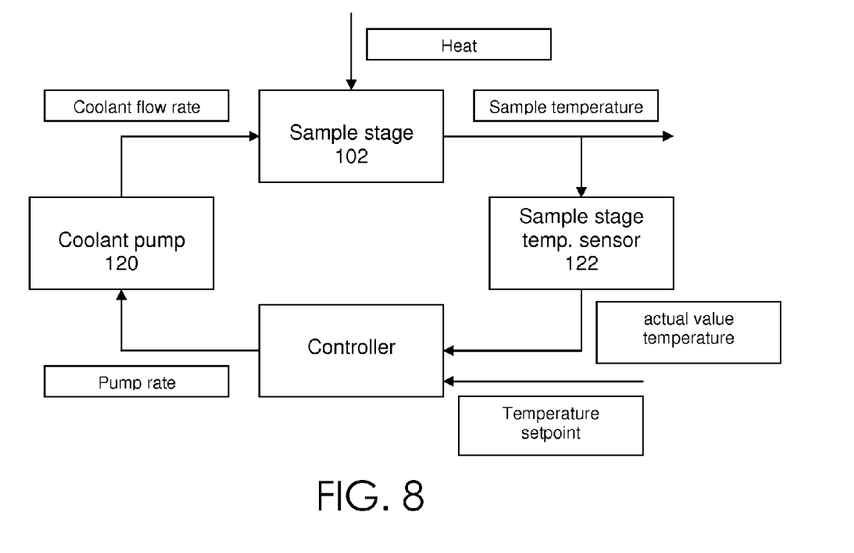
FIG. 8 shows a first variant of a block diagram of a control loop for regulating the temperature of the sample.

FIG. 8 shows a first variant of a block diagram of a control loop for regulating the temperature of the sample. In this variant, sample stage 102 has associated with it a temperature sensor 122 (Temp. sensor 122) that measures the actual value of the sample temperature. The controller regulates the temperature of the cooled sample stage, by way of the pump rotation speed (Pump rate), to a setpoint temperature definable by the operator. The temperature of sample stage 102 is thus regulated by way of the flow rate of liquid nitrogen through cooling finger 105.

Figure 9:
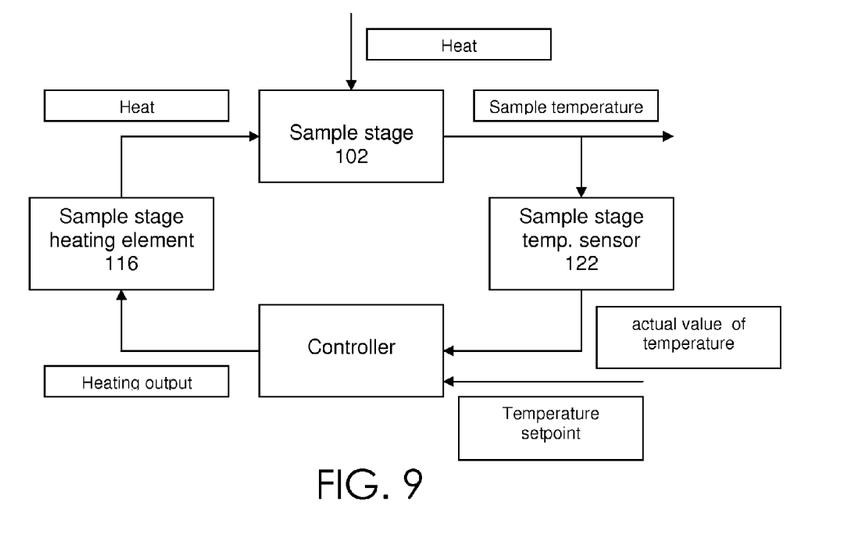
FIG. 9 shows a second variant of a block diagram of a control loop for regulating the temperature of the sample.

FIG. 9 shows a second variant of a block diagram of a control loop for regulating the temperature of the sample. With this variant as well, sample stage 102 has associated with it a temperature sensor 122 (Temp. sensor 122) that measures the actual value of the sample temperature. Furthermore, a heating element 116 is additionally associated with sample stage 102. The controller regulates the temperature of the cooled sample stage 102, with the aid of heating element 116, to a setpoint temperature definable by the operator. As already mentioned above, the advantage of the second variant with respect to the first variant is that desired changes in temperature can be reacted to more quickly.

Figure 10:
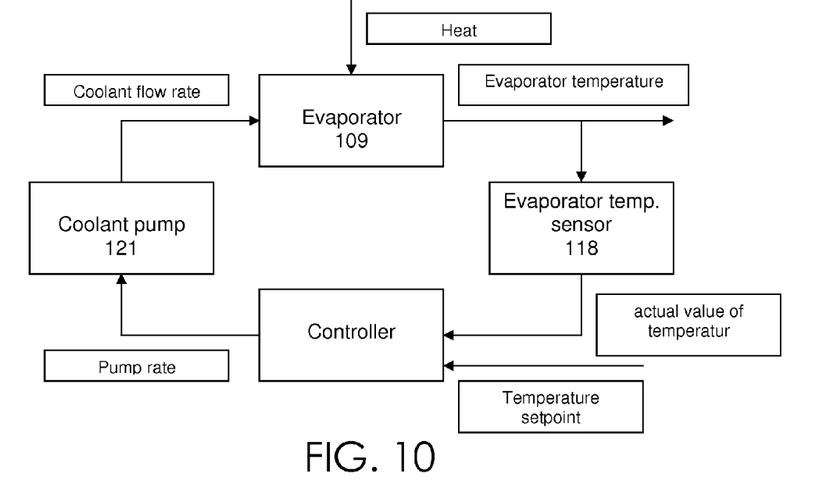
FIG. 10 is a block diagram of a control loop for regulating the temperature of the evaporator block.

FIG. 10 is a block diagram of a control loop for regulating the temperature of evaporator block 109. Evaporator block 109 has associated with it a temperature sensor 118 (Temp. sensor 118) that measures the actual value of the evaporator block temperature. The controller regulates the temperature of the cooled evaporator block 109, by way of the pump rotation speed (Pump rate) of coolant pump 121, to a setpoint temperature definable by the operator. The temperature of evaporator block 109 is thus regulated by way of the flow rate of liquid nitrogen through cooling finger 105. In particular, the temperature of evaporator block 109 is regulated by means of the pump rotation speed of the coolant pump so that it is held just below the flow temperature of the coolant in the form of liquid nitrogen, i.e. between approximately 190° C. and −195° C., so that the coolant emerges from outlet 117 of evaporator block 109 only in gaseous form.

Figure 11:
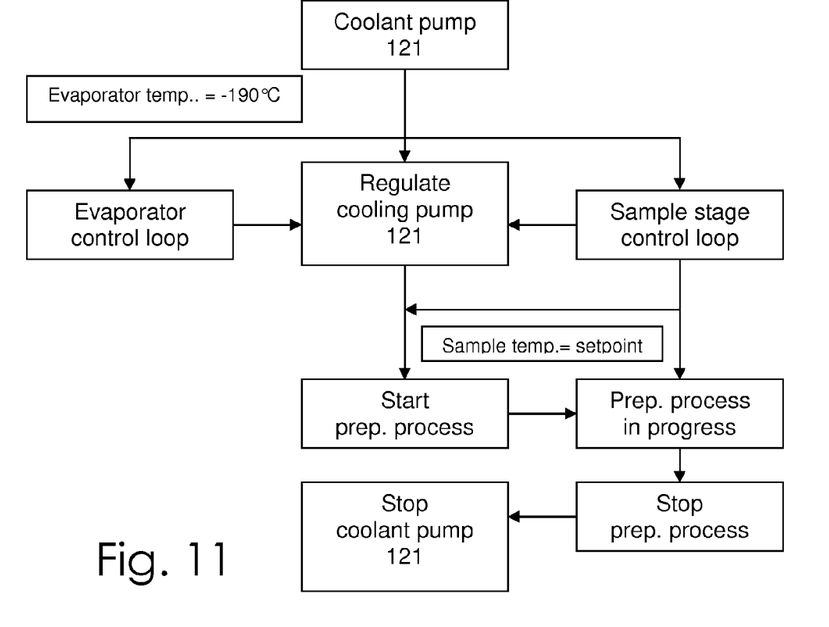
FIG. 11 is a block diagram depicting the control sequence for cooling.

FIG. 11 is a block diagram depicting the control sequence for cooling. At the beginning of the cooling operation, the coolant pump is activated (Start coolant pump). The temperature of sample stage 102 (Sample stage control loop; see FIG. 6) and of evaporator block 109 (Evaporator control loop; see FIG. 8) are regulated, by way of the pump rotation speed of coolant pump 121 (Regulate coolant pump) to a setpoint temperature definable by the operator, as described earlier in FIG. 6 and FIG. 8. To begin (Start prep. process), the sample is cooled to a desired temperature. Only when that has been reached is an automatic authorization given for the ion beam etching preparation process (Prep. process in progress). As soon as the preparation process is complete (Stop prep. process), cooling is stopped by deactivating the coolant pump (Stop coolant pump).

Figure 12:
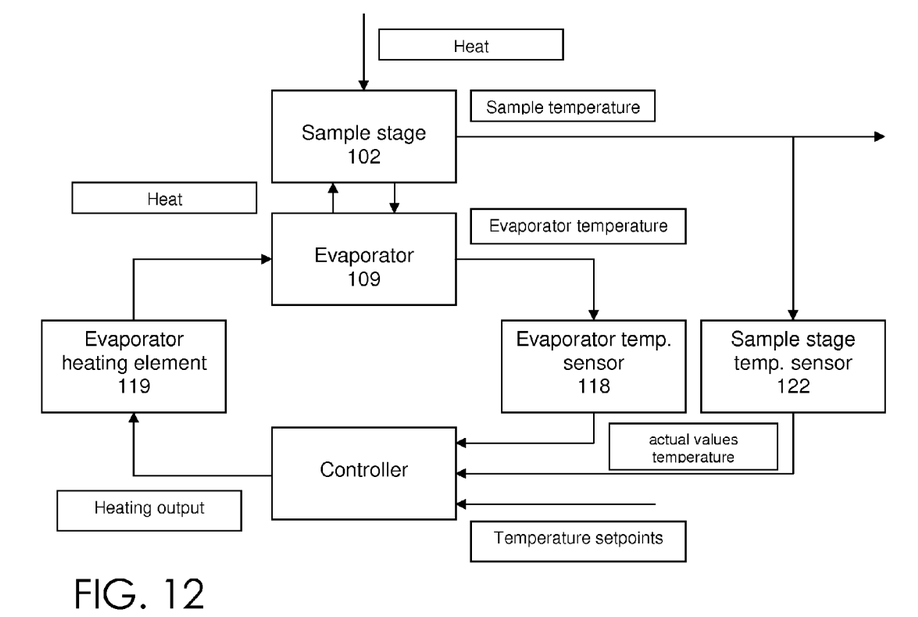
FIG. 12 is a block diagram of a control loop for regulating the temperature upon heating after completion of the ion beam etching operation.
Figure 13:
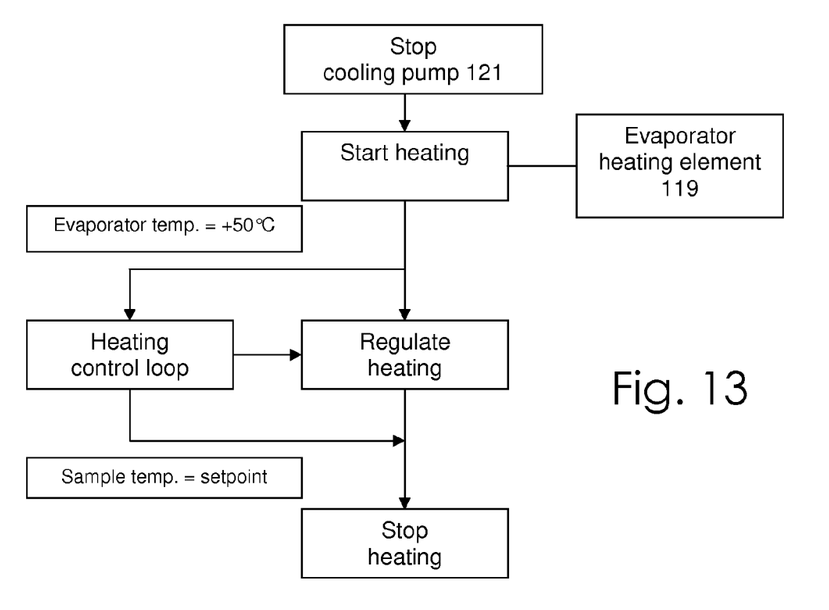
FIG. 13 is a block diagram depicting the control sequence for heating.

FIG. 12 shows a block diagram of a control loop for regulating temperature during heating once the ion beam etching operation has ended, and FIG. 13 shows a block diagram of the control sequence for heating by means of the control loop depicted in FIG. 12. The description that follows refers to FIG. 12 and FIG. 13. The evaporator block has associated with it a heating element 119 that serves exclusively to heat up the entire sample stage flange 100 (e.g. including sample stage 102, mask holder 103, and evaporator block 109), but not to regulate temperature during the ion beam etching operation. The control loop depicted in FIG. 10 serves to monitor and regulate the controlled heating operation in order to prevent condensation of atmospheric moisture from ambient air onto the sample. Before heating, cooling is stopped by deactivating the coolant pump (Stop coolant pump). Heating is started by switching on heating element 119 (Start heating). Heating element 119 heats, with maximum heat output, evaporator block 109 and also, via the connection of the cooling finger, sample stage 102 along with the sample, and mask holder 103 along with mask 104. Because heating element 119 is arranged directly in evaporator block 109, the latter heats up more quickly than sample stage 102 and mask holder 103 located farther away. Once evaporator block 109 reaches a temperature of +50° C. (measured by means of a temperature sensor on evaporator block 109), the temperature is then regulated by means of the controller (Regulate heating). In this context, the controller holds the temperature of evaporator block 109 constant by throttling the heat output of heating element 119. Sample stage 102 and mask holder 103 are further heated until reaching their setpoint temperature, which usefully is room temperature (measured by means of the temperature sensor on sample stage 102). Once the setpoint temperature of sample stage 102 and mask holder 103 has been reached, heating is terminated (Stop heating), and sample stage flange 100 can be aerated and opened for sample removal.

The temperature of mask holder 103 is not additionally regulated, since mask holder 103 exhibits a temperature behavior during cooling and heating that is approximately identical to that of sample stage 102. The temperature of mask holder 103 is thus coupled to the regulation of the temperature of the sample stage, and is consequently not additionally monitored.

In addition, the coolant level in the reservoir receptacle (Dewar vessel) is monitored. If the level is too low, a warning is provided to the operator. This warning can occur optically and/or acoustically. If the fill level drops below a critical value, the cooling process is interrupted or cannot be started.

The invention is not to be limited to the specific embodiments disclosed, and modifications and other embodiments are intended to be included within the scope of the invention.

What is claimed is:

1. A cooling apparatus (101) for a sample in an ion beam etching process, comprising:
   a sample stage (102) for receiving the sample;
   a coolant receptacle (120) containing a coolant;
   a cooling finger (105) connectable to the coolant receptacle (120), the cooling finger (105) including a conduit (130, 131) through which the coolant can flow when the cooling finger is connected to the coolant receptacle (120);
   at least one thermal conduction element (106a, 106b) connecting the sample stage (102) to the coolant in the cooling finger (105) in heat-transmitting fashion such that heat is transferred from the sample stage (102) to the coolant, wherein the thermal conduction element is fabricated of a metal;
   an evaporator block (109) for evaporating the coolant flowing out of the cooling finger (105), wherein the conduit (130, 131) of the cooling finger (105) opens into the evaporator block (109);
   a heating element (119) for heating at least the evaporator block (109); and
   a temperature regulation device for regulating the temperature of the evaporator block (109), wherein a signal corresponding to the temperature of the evaporator block is delivered to the temperature regulation device and the temperature regulation device regulates the temperature of the evaporator block (109) to a definable value, wherein the temperature regulation device is operable to regulate the temperature of the sample stage (102) and the temperature of the evaporator block (109) with the heating element (119) to a temperature value at which condensation of atmospheric moisture from ambient air onto the sample is prevented after completion of the ion beam etching operation.

2. The cooling apparatus according to claim 1, further comprising a means (121) for controlling the coolant flow.

3. The cooling apparatus according to claim 2, wherein the means for controlling the coolant flow includes a coolant pump (121).

4. The cooling apparatus according claim 1, wherein the cooling finger (105) has an outer wall and an inner wall spaced from the outer wall.

5. The cooling apparatus according claim 1, further comprising:
   a mask holder device (103);
   a mask (104) held by the mask holder device (103), the sample being positionable relative to the mask; and
   at least one further thermal conduction element (106c) extending from the cooling finger (105) to the mask holder device (103).

6. The cooling apparatus according to claim 1, further comprising:
   a temperature measuring means (118) for measuring the temperature of the evaporator block (109).

7. The cooling apparatus according claim 1, further comprising at least one of:
   a temperature measuring means (122) for measuring the temperature of the sample stage (102); and
   a heating element (116) for heating the sample stage (102).

8. The cooling apparatus according to claim 7, wherein a signal corresponding to the temperature of the sample stage is delivered to the temperature regulation device and the temperature regulation device regulates the temperature of the sample stage (102) to a second definable value.

9. The cooling apparatus according to claim 8, further comprising a heating element (116) associated with the sample stage (102), wherein the temperature regulation device regulates the temperature of the sample stage (102) to the definable value via the heating element (116).

10. The cooling apparatus according to claim 1, further comprising a coolant pump (121) for controlling the coolant flow, wherein the temperature regulation device regulates the temperature of the evaporator block (109) to the definable value by adjusting a pump rotation speed of the coolant pump (121).

11. The cooling apparatus according to claim 8, further comprising a coolant pump (121) for controlling the coolant flow, wherein the temperature regulation device regulates the temperature of the sample stage (102) to the second definable value by adjusting a pump rotation speed of the coolant pump (121).

12. A method for adjusting temperature of a sample in an ion beam etching operation, comprising the steps of:
   (a) mounting a sample on a coolable sample stage (102) of an ion beam etching apparatus, the sample stage (102) having a cooling apparatus associated therewith comprising a coolant receptacle (120) containing a coolant, a cooling finger (105) connectable to the coolant receptacle (120) and including a conduit (130, 131) through which the coolant can flow when the cooling finger is connected to the coolant receptacle (120), and at least one thermal conduction element (106a, 106b) fabricated of a metal connecting the sample stage (102) to the coolant in the cooling finger (105) in heat-transmitting fashion such that heat is transferred from the sample stage (102) to the coolant;
   (b) aligning the sample on the sample stage (102); and (c) cooling the sample by directing the coolant through the conduit (130, 131) of the cooling finger (105) to establish a desired temperature for the ion beam etching operation, wherein the coolant is a liquefied gas and wherein the conduit (130, 131) of the cooling finger (105) opens into an evaporator block (109) for evaporating the coolant flowing out of the cooling finger (105), and wherein a flow rate of the coolant is adjusted so that the coolant flowing through the evaporator block (109) emerges from the evaporator block (109) in gaseous form.

13. The method according to claim 12, further comprising the step of:

(d) terminating the cooling of the sample after termination of the ion beam etching operation.

14. The method according to claim 13, further comprising the step of:

(e) heating the sample to a temperature at which condensation of atmospheric moisture from ambient air onto the sample is prevented after step (d).

15. The method according to claim 14, wherein the sample is aligned relative to a mask (104), the mask (104) being cooled and heated along with the cooling of the sample in step (c) and the heating of the sample in step (e).

16. The method according to claim 12, wherein the desired temperature is held constant during the ion beam etching operation.

17. The method according to claim 12, wherein the coolant is selected from the group of coolants consisting of liquid nitrogen and liquid air.

18. A cooling apparatus (101) for a sample in an ion beam etching process, comprising:

a sample stage (102) for receiving the sample;

a coolant receptacle (120) containing a coolant;

a cooling finger (105) connectable to the coolant receptacle (120), the cooling finger (105) including a conduit (130, 131) through which the coolant can flow when the cooling finger is connected to the coolant receptacle (120);

at least one thermal conduction element (106*a*, 106*b*) connecting the sample stage (102) to the coolant in the cooling finger (105) in heat-transmitting fashion such that heat is transferred from the sample stage (102) to the coolant;

a mask holder device (103);

a mask (104) held by the mask holder device (103), the sample being positionable relative to the mask; and at least one further thermal conduction element (106*c*) extending from the cooling finger (105) to the mask holder device (103), wherein the thermal conduction elements are fabricated of a metal that is in direct contact with the cooling finger.

* * * * *